United States Patent [19]

Addicks et al.

[11] Patent Number: 5,041,430
[45] Date of Patent: Aug. 20, 1991

[54] ORAL ANTICOAGULANT/PLATELET INHIBITOR LOW DOSE FORMULATION

[75] Inventors: William J. Addicks, Wilmington; Joseph A. Mollica, Rockland, both of Del.; Gary H. Slatko, Chadds Ford, Pa.

[73] Assignee: Du Pont Mereck Pharmaceutical Company, Wilmington, Del.

[21] Appl. No.: 408,394

[22] Filed: Sep. 18, 1989

[51] Int. Cl.$^5$ .................. A61K 31/35; A61K 31/40; A61K 31/44; A61K 31/54; A61K 31/62; A61K 31/415
[52] U.S. Cl. .................. 514/161; 514/226.5; 514/301; 514/404; 514/420; 514/457
[58] Field of Search ............ 514/161, 457, 822, 226.5, 514/420, 301, 404

[56] References Cited

U.S. PATENT DOCUMENTS 4,444,777 4/1984 Fleming et al. ............... 514/822
4,537,894 8/1985 Blanchard et al. ............. 514/301

FOREIGN PATENT DOCUMENTS 0001503 4/1979 European Pat. Off. .
2265273 10/1975 France .
2390959 1/1979 France .

Primary Examiner—Stanley J. Friedman

[57] ABSTRACT

There are disclosed combination products useful for the treatment and/or prevention of a first or recurrent myocardial infarction or a first or recurrent stroke. Said combination products comprise low doses of an oral anticoagulant, preferably warfarin and platelet inhibiting agents, including non-steroidal antiinflammatory agents and preferrably aspirin.

24 Claims, No Drawings

ORAL ANTICOAGULANT/PLATELET INHIBITOR LOW DOSE FORMULATION

BACKGROUND OF THE INVENTION

1. Field of Invention

This invention relates to combination products comprising low doses of oral anticoagulants, such as warfarin, and low doses of inhibitors of platelet function (e.g., aggregation, adhesion) such as non-steroidal antiinflammatory agents, and preferably aspirin, in a single dosage form. Further, this invention relates to methods of using these low dose combination products for the prevention and/or treatment of first or recurrent myocardial infarction or the prevention and/or treatment of first or recurrent stroke.

2. Background Information

Recent advances in the understanding of the pathogenic factors leading to the acute coronary ischemic syndromes of unstable angina, myocardial infarction and ischemic sudden death, and acute cerebrovascular ischemic syndromes like transient ischemic attacks and stroke have demonstrated the individual importance of two compounds in particular, acetyl salicylic acid, hereinafter referred to as aspirin or ASA, and warfarin, in the prevention and/or treatment of these syndromes. Recently the value of antithrombotic therapy with high-dose aspirin in unstable angina has been conclusively demonstrated by two randomized, placebo-controlled, double-blind trials. See generally Lewis, et al. "Protective Effects of Aspirin Against Acute Myocardial Infarction and Death in Men with Aspirin " Results of a Veterans Cooperative Study, *New England Journal of Medicine*, 309: 396 (1983) and Cairns, et al.: "Aspirin, Sulfinpyrazone or Both in Unstable Angina: Results of a Canadian Multicenter Trial". *New England Journal of Medicine*, 313: 1369, (1985). Also, the recently pooled results of several studies suggest that long-term high-dose oral anticoagulant therapy may reduce the rate of recurrence of myocardial infarction by about 20%. [Fuster, et. al, (1988) *Perspective*, "Insights into the Pathogenesis of Acute Ischemic Syndromes", 77, No. 6, pp 1213–1220].

Since currently available pharmaceutical products have an isolated inhibitory effect on either platelet function or thrombus formation, the use of a combination of agents which would effect both platelet aggregation/adhesion and thrombus formation simultaneously, provides a potential benefit of improved efficacy at lower dosages over the use of individual agents. Since aspirin may prevent ischemic cardiac events caused by coronary artery disease and oral anticoagulants may protect against both ischemic cardiac events and resultant cerebral embolization from ventricular thrombi, the combination in small doses may provide the best overall protection. [Fuster, V., Halperin, J. L., (1989) *The New England Journal of Medicine*, Feb. 9, 1989, pp 392–394.]

Traditionally, the simultaneous use of warfarin and aspirin at high doses has been relatively contraindicated. It has been a pervasive practice in the medical community to use these agents on an either/or basis. This practice was largely due to medical literature reporting undesirable clinical and pharmacologic interactions of the two drugs at high doses. Clinically, the propensity of aspirin, at high doses, to cause gastric mucosal erosion/ulceration, when dosed with an oral anticoagulant (warfarin) has led to a high reported incidence of exaggerated gastrointestinal (GI) bleeding with the high dose combination. Pharmacologically, aspirin at high doses also acts synergistically with warfarin to elevate the prothrombin time assay level for a given dose of warfarin. In light of recent advances in the study of the acute coronary syndromes and the recognition of the individual benefits that aspirin and warfarin provide in treating and/or preventing these syndromes, there is a need for a combination product wherein an oral anticoagulant such as warfarin and an antiplatelet agent, such as aspirin or a non-aspirin-non-steroidal antiinflammatory agent are present in a low dose ratio. The combination permits the use of doses below those currently accepted as "therapeutic" in the medical literature, in other words, doses at which the beneficial effects of the two agents are favored over the dose related side effects associated with simultaneous administration of currently accepted, high doses of the two agents.

SUMMARY OF THE INVENTION

There are provided pharmaceutical compositions comprising an oral anticoagulant such as warfarin and a platelet inhibitor such as a non-steroidal antiinflammatory drug (NSAID) and more particularly a composition wherein the non-steroidal antiinflammatory drug is aspirin. The pharmaceutical compositions of this invention are combination products with low doses of each drug component. Further provided are pharmaceutical compositions comprising low doses of warfarin and a platelet inhibiting drug such as ticlopidine or other agents such as thromboxane receptor antagonists or thromboxane synthetase inhibitor compounds. Still further provided is a method of using the pharmaceutical compositions of this invention for preventing and/or treating a first or recurrent myocardial infarction or first or recurrent stroke, in a mammal.

DETAILED DESCRIPTION

The present invention is a pharmaceutical combination composition comprising warfarin present in an amount to be delivered of about 0.5 mg–10 mg and aspirin present in an amount to be delivered of about 10–500 mg. "Warfarin" as used herein means crystalline warfarin as well as amorphous sodium warfarin and derivatives thereof. Preferred compositions comprise warfarin present in an amount to be delivered of about 1–7.5 mg and aspirin present in an amount to be delivered of about 20–325 mg. The most preferred embodiments of the present invention comprise warfarin present in an amount to be delivered of about 1–5 mg and aspirin present in an amount to be delivered of about 40–162.5 mg.

Although aspirin is the preferred platelet inhibitory agent of the present invention, other non-aspirin, non-steroidal antiinflammatory agents that inhibit platelet function such as ibuprofen, naproxen, sulindac, indomethacin, mefenamate, droxicam, diclofenac, sulfinpyrazone and piroxicam, in combination with warfarin, are within the scope of this invention. Of the non-aspirin, non-steroidal antiinflammatory drugs (NSAIDS), a preferred embodiment of the present invention comprises warfarin and piroxicam, commercially available from Pfizer, as Feldene®, since piroxicam exerts an antiplatelet effect when dosed once daily. Preferably, a combination of piroxicam and warfarin comprises warfarin present in an amount to be delivered of about 0.5 mg-10 mg and piroxicam present in an amount to be delivered of about 5-50 mg. More preferably the combination would contain warfarin present in an amount to be delivered of about 1-7.5 mg and piroxicam present in an amount to be delivered of about 10-40 mg. The most preferred embodiment comprises warfarin present in an amount to be delivered of about 1-5 mg and piroxicam present in an amount to be delivered of about 10-20 mg.

Other embodiments of this invention include the following NSAIDs present in the amount shown along with warfarin in the amount shown.

| Indomethacin | Warfarin |
|---|---|
| 20-100 mg | 0.5-10 mg |
| Naproxen | Warfarin |
| 20-100 mg | 0.5-10 mg |
| Droxicam | Warfarin |
| 20-100 mg | 0.5-10 mg |
| Diclofenac | Warfarin |
| 20-100 mg | 0.5-10 mg |
| Sulfinpyrazone | Warfarin |
| 20-100 mg | 0.5-10 mg |

More preferably the NSAIDs listed above are present in an amount of about 25-90 mg and warfarin is present in an amount of about 1-7.5 mg. The most preferred embodiment of non-aspirin-NSAIDs and warfarin comprises the NSAIDs listed above present in an amount of about 25-75 mg and warfarin present in an amount of about 1-5 mg.

Another embodiment of this invention includes other platelet inhibiting or thromboxane inhibiting compounds such as ticlopidine, in combination with warfarin. Platelet inhibitors such as ticlopidine are not associated with the GI irritation that aspirin and other nonsteroidal antiinflammatory agents may exhibit and therefore may be a more acceptable dosage form in individuals with a history of GI problems such as ulceration. Furthermore, such a combination would be useful in a patient having a sensitivity to aspirin or other nonsteroidal antiinflammatory agents. Preferably a combination of ticlopidine and warfarin comprises warfarin present in an amount to be delivered of about 0.5-10 mg and ticlopidine present in an amount to be delivered of about 100-750 mg. More preferably, the combination comprises warfarin present in an amount to be delivered of about 1-7.5 mg and ticlopidine present in an amount to be delivered of about 200-600 mg. The most preferred embodiment comprises warfarin present in an amount to be delivered of about 1-5 mg and ticlopidine is present in an amount to be delivered of about 250-500 mg.

Other platelet aggregation or adhesion inhibitory agents such as thromboxane-$A_2$-receptor antagonists and thromboxane-$A_2$-synthetase inhibitors are also useful in the present invention.

The combination products of the present invention can be in any dosage form known to those skilled in the art, such as tablets either single or multi-layered, capsules, caplets, liquids, or suppositories. The preferred dosage forms are tablets, capsules and caplets. These preferred dosage forms can be made by methods known to those skilled in the art and described in Reminoton's Pharmaceutical Sciences, (1985), 17th Edition, Osol, a standard reference in the field.

Due to the nature of the preferred compounds of this invention, warfarin and aspirin, the potential exists for a chemical interaction between warfarin and aspirin formulated in a single dosage form. This potential is evidenced by results of compatibility experiments in which aspirin and sodium warfarin were intimately mixed in the ratio of 1 part sodium warfarin to 80 parts aspirin and stored at room temperature, 60° C., or under 600 foot-candles of light. Results recorded as average % recovery (±s.d.) are shown in Table I.

TABLE I

| | Aspirin And Sodium Warfarin Solid State Stability After One Week | | |
|---|---|---|---|
| Condition | Aspirin Recovery Where Aspirin Is Stored Alone | Aspirin Recovery Where Aspirin Is Mixed* With Sodium Warfarin | Sodium Warfarin Recovery Where Sodium Warfarin Is Mixed* With Aspirin |
| room temperature (22° C.) | 101.1 (0.5) | 100.5 (0.5) | 99.6 (1.8) |
| 60° C. | 99.8 (1.6) | 76.6 (2.9) | 72.8 (3.31) |
| 600 F-C | 100.9 (1.0) | 94.1 (2.7) | 88.8 (9.5) |

*mixed at a ratio of 1 part sodium warfarin to 80 parts aspirin

For this reason, the preferred dosage forms of this invention are formulated such that the physical contact between the warfarin and the aspirin is minimized. In order to minimize the contact between the warfarin and aspirin components, one embodiment of this invention provides for a combination product wherein the aspirin component is enteric coated. By enteric coating the aspirin, it is possible not only to minimize the contact between the two active ingredients, but also, it is possible to control the release of the aspirin in the GI tract such that the aspirin is not released in the stomach but rather is released in the intestines. Such a formulation will further reduce the risk of GI side effects associated with aspirin since not only will the aspirin be present in a low dose, but also, it will be enteric coated thereby releasing lower in the GI tract.

Another embodiment of this invention provides for a combination product wherein the aspirin is coated with a sustained-release material which effects a sustained release throughout the gastrointestinal tract and also serves to minimize physical contact between aspirin and warfarin. Furthermore, the sustained release aspirin can be additionally enteric coated such that aspirin release occurs only in the intestine.

Still another approach would involve the formulation of a combination product in which the aspirin component is coated with a sustained and/or enteric release polymer, and the warfarin particles or granules are also coated with a polymer such as a low-viscosity grade of hydroxypropyl methylcellulose (HPMC) or other appropriate materials as known in the art in order to further separate the active components. The warfarin can alternatively be dry granulated with appropriate excipients, and the resulting granules are then coated with HPMC. The coating of the warfarin component serves to form an additional barrier to interaction with aspirin.

Dosage forms of the present invention wherein the aspirin component is enteric coated can be in the form of tablets such that the enteric coated aspirin and the warfarin are blended together and then compressed into a tablet or such that the enteric coated aspirin is compressed into one tablet layer and the warfarin is compressed into an additional layer. Optionally, in order to further separate the two layers, one or more placebo layers may be present such that the placebo layer is between the warfarin layer and aspirin layer.

In addition, dosage forms of the present invention can be in the form of capsules wherein the aspirin component is compressed into a tablet or preferably the aspirin component is in the form of a plurality of microtablets, particles, granules or non-pareils, which are then enteric coated. These enteric coated microtablets, particles, granules or non-pareils are then placed into a capsule or compressed into a capsule along with the warfarin granulation. Conversely, the warfarin component can be made into a tablet or microtablets and placed into a capsule along with a powder blend consisting of enteric or sustained release aspirin present as coated particles, granules or non-pareils.

Further embodiments of this invention comprise a sustained release dosage form in which aspirin is formulated in such a way as to be delivered over 3-12 hours. The aspirin can alternatively be formulated to effect a 3-12 hour delivery in the intestine only.

The formulations of the present invention may comprise, in addition to active ingredients, appropriate excipients, including but not limited to: lubricants such as magnesium stearate, stearic acid, sodium stearyl fumarate, and hydrogenated vegetable oil; diluents such as lactose, microcrystalline cellulose, dextrose, starch and dicalcium phosphate; a glidant such as colloidal silicon dioxide; and disintegrates such as sodium starch glycolate and croscarmellose sodium. The use of such excipients is known to those skilled in the art of pharmaceutical formulations.

The following examples describe various formulations of warfarin and aspirin combination products. These formulations are merely exemplary, it being understood that those skilled in the art can make obvious modifications thereof.

I. Immediate Aspirin Release Within the Intestine

1. Enteric-Coated Aspirin/Sodium Warfarin

The following strategies can be utilized to achieve a product yielding the delivery of drug directly to the intestine whereupon it is immediately released, as well as a physical separation of sodium warfarin and aspirin.

A. Enteric Coated Aspirin Blended with Sodium Warfarin

Aspirin particles, granules, or non-pareils are enteric coated with either a solvent-based or water-based enteric coating polymer, using a fluidized-bed process, a pan-coating process, a solids processor, or other methods known in the art. Examples of enteric coatings which can be used are cellulose acetate phthalate (Aquateric®, FMC Corp.) and various methacrylic acid copolymers (Eudragit®L30D, Eudragit®L and/or Eudragit®S, available from Röhm Pharma.), and other enteric coat materials as known in the art. Eudragit®L30D may be used alone or in combination with Eudragit®NE 30D (a methacrylate ester copolymer available from Röhm Pharma). For the cases in which the coating process is carried out using an aqueous-based solvent, a thin subcoat of hydroxypropyl methylcellulose may be used. The coating layer serves to minimize contact between the aspirin and sodium warfarin within the dosage form, in addition to effecting aspirin delivery to the intestine. These coated particles, granules, or non-pareils are then blended with sodium warfarin and appropriate excipients, and this mixture is subsequently either tableted or encapsulated. Following is an example of a formulation of this type:

EXAMPLE 1

Enteric Coated Aspirin Blended With Sodium Warfarin

| Component | Amount (mg) per Dosage Unit |
|---|---|
| Aspirin coated with 9-25% Eudragit ® L 30D | 549.45-666.66 (500 mg active) |
| Sodium Warfarin | 1.0 |
| Microcrystalline Cellulose | 82.74-199.95 |
| Sodium Starch Glycolate | 32.0 |
| Colloidal Silica | 1.6 |
| Sodium Stearyl Fumarate | 16.0 |
| To Total | 800.0 mg |

Prior to weighing, pass all ingredients through an appropriate screen as needed. Weigh all ingredients and mix the sodium warfarin with the colloidal silica, sodium starch glycolate and one-half of the microcrystalline cellulose for about 15 minutes in a twin-shell blender. Add one-half of the sodium stearyl fumarate and mix for about 3 minutes. Slug this blend using ½ inch flat-face punches and mill. Add the aspirin to the remaining microcrystalline cellulose and mix for about 15 minutes. Add this blend to the sodium warfarin granulation and mix for about 7 minutes. Add the remaining sodium strearyl fumarate, mix for about 3 minutes, and compress into tablets. It should be noted that the microcrystalline cellulose in this formulation is adjusted such that the total dosage form weight is 800.0 mg.

EXAMPLE 2

Enteric Coated Aspirin Blended With Sodium Warfarin

| Component | Amount (mg) per Dosage Unit |
|---|---|
| Aspirin coated with 9.4% Eudragit ® L30D (2% hydroxypropyl methylcellulose subcoat) | 180.59 (160 mg active) |
| Starch | 100.16 |
| Sodium Warfarin | 1.0 |
| Microcrystalline Cellulose | 196.0 |
| Sodium Starch Glycolate | 20.0 |
| Colloidal Silica | 1.0 |
| Magnesium Stearate | 1.25 |
| To Total | 500.0 mg |

Prior to weighing, pass all ingredients through an appropriate screen as needed. Weigh all ingredients and mix the sodium warfarin with the colloidal silica, starch, sodium starch glycolate and one-half of the microcrystalline cellulose for about 15 minutes in a twin-shell blender. Add one-half the magnesium stearate and blend for about 3 minutes. Slug this blend using ½ inch flat-face punches and mill. Add the aspirin to the remaining microcrystalline cellulose and blend for about 15 minutes. Add this blend to the sodium warfarin granulation, and blend for about 7 minutes. Add the remaining magnesium stearate, mix for about 3 minutes, and compress into tablets or alternatively, place into capsules.

Using this formula and manufacturing directions, 7/16 inch tablets were produced, having a hardness of 8-10 Strong-Cobb Units (SCU). Dissolution tests were performed for both drugs in accordance with the dissolution tests for enteric coated aspirin tablets and sodium warfarin tablets as described in the United States Pharmacopeia/National Formula (USP/NF) XVII. For aspirin, dissolution was carried out by placing tablets in baskets rotating at 100 rpm. The dissolution media consisted of 750 ml of 0.1 N HCl (37° C.) for the first two hours of the test, followed by the addition of 250 ml of 0.2 N Tribasic sodium phosphate for a resulting pH of 6.8 during the remainder of the test. All analysis was by reversed-phase high performance liquid chromatography (HPLC). Results of aspirin dissolution are shown in Table II.

TABLE II

Aspirin Dissolution From Tablets Manufactured In Accordance With Example 2

| Time (min) | pH | Average (n = 3) % Dissolved |
| --- | --- | --- |
| 60 | 1.0 | 0.7 |
| 120 | 1.0 | 1.6 |
| 180 | 6.8 | 100.3 |
| 210 | 6.8 | 100.7 |

These tablets pass the criteria outlined in USP/NF XVII for enteric release aspirin tablets (less than 10% aspirin released after 120 minutes at pH 1.0, greater than 80% released after 90 minutes at pH 6.8).

Sodium warfarin dissolution was assessed by placing tablets in 900 ml of pH 7.5-phosphate buffer maintained at 37° C., using a paddle at 50 rpm. An average of three tablets yielded 91.3% sodium warfarin release in 30 minutes, which passes the specifications as set forth in USP/NF XVII (not less than 80% release in 30 minutes).

B. Enteric Coated Aspirin Compressed in a Multilayer Tablet

This approach serves to greatly minimize the drugs' area of contact. Aspirin particles, granules, or nonpareils are first enteric coated as specified in I-lA. The enteric coated aspirin is blended with appropriate excipients, and the sodium warfarin is dry granulated with the same excipients. The aspirin blend is then compressed, and the sodium warfarin layer is subsequently compressed onto this layer. These two drug layers may optionally be further separated by an additional placebo layer. Following is an example of a formulation of this type:

EXAMPLE 3

Enteric Coated Aspirin/Sodium Warfarin Into A Multilayer Tablet

| Component | Amount (mg) per Dosage Unit |
| --- | --- |
| Aspirin coated with 9-25% Eudragit ® L30D | 43.96-53.33 (40.0 mg active) |
| Sodium Warfarin | 5.0 |
| Lactose | 324.62-333.99 |
| Sodium Stearyl Fumarate | 8.0 |
| Tapioca Starch, Pregelatinized | 9.05 |
| To Total | 400.0 mg |

Prior to weighing, pass all ingredients through an appropriate screen as needed. Weigh all ingredients and combine the sodium warfarin with one-half of the tapioca starch and lactose. Mix in a twin-shell blender for about 15 minutes. Add one-fourth of the sodium stearyl fumarate and mix for about 3 minutes. Slug this blend using ½ inch flat-face punches and mill. Add one-fourth of the sodium stearyl fumarate and mix for about 3 minutes. Mix the aspirin with the remainder of the lactose and tapioca starch for about 10 minutes in a twin-shell blender. Add the remaining sodium stearyl fumarate and mix for about 3 minutes. Using a multilayer tablet machine such as the Manesty Layer Press available from Thomas Engineering, compress the aspirin blend, followed by the sodium warfarin granulation, to produce a bilayer tablet. It should be noted that the lactose in this formulation is adjusted such that the total dosage form weight is 400.0 mg.

C. Enteric Coated Aspirin Tablet Within a Capsule

This formulation involves the manufacture of an aspirin tablet or aspirin microtablets which are then enteric coated and placed into a capsule along with a sodium warfarin granulation. Following is an example of a formulation of this type:

EXAMPLE 4

Enteric Coated Aspirin Tablet/ Sodium Warfarin Blend Within A Capsule

| Component | Amount (mg) per Dosage Unit |
| --- | --- |
| Aspirin | 40.0 |
| Eudragit ® L30D | 24.0 |
| Sodium Warfarin | 1.0 |
| Lactose | 106.5 |
| Microcrystalline Cellulose | 39.0 |
| Dicalcium Phosphate | 184.5 |
| Croscarmellose Sodium | 16.0 |
| Colloidal Silica | 1.0 |
| Hydrogenated Vegetable Oil | 12.0 |
| To Total | 424.00 mg |

Prior to weighing, pass all ingredients through an appropriate screen as needed. Weigh all ingredients and mix the aspirin with the lactose, microcrystalline cellulose and one-half of the colloidal silica and croscarmellose sodium for about 15 minutes in a twin-shell blender. Add one-half of the hydrogenated vegetable oil and mix for about 5 minutes. Compress this blend into tablets, and coat these with Eudragit ®L30D using an appropriate method known in the art. Mix the sodium warfarin with the dicalcium phosphate and the remaining colloidal silica and croscarmellose sodium for about 15 minutes. Add one-fourth of the hydrogenated vegetable oil and mix for about 5 minutes. Slug this blend using ½ inch flat-face punches and mill. Add the remaining hydrogenated vegetable oil and mix for about 5 minutes. Encapsulate this formulation with the use of a capsule filling machine such as the Zanasi AZ5, commercially available from Soteco USA, Inc., by placing 200 mg of the sodium warfarin granulation and one aspirin tablet into each capsule.

EXAMPLE 5

Sodium Warfarin Tablet/Enteric Coated Aspirin Blend Within A Capsule

| Component | Amount (mg) per Dosage Unit |
| --- | --- |
| Aspirin coated with 9-25% Eudragit ® L30D | 82.42-100.0 (75 mg active) |
| Sodium Warfarin | 10.0 |
| Lactose | 57.5-75.08 |
| Microcrystalline Cellulose | 20.0 |
| Sodium Starch glycolate | 8.0 |
| Colloidal Silica | 0.5 |
| Sodium Stearyl Fumarate | 4.0 |

| Component | Amount (mg) per Dosage Unit |
| --- | --- |
| To Total | 200.00 mg |

Prior to weighing, pass all ingredients though an appropriate screen as needed. Weight all ingredients and mix the aspirin with one-half of the lactose, sodium starch glycolate and colloidal silica for about 15 minutes in a twin-shell blender. Add one-half of the sodium stearyl fumarate and mix for about 5 minutes. Combine the sodium warfarin with the microcrystalline cellulose and the remaining lactose, sodium starch glycolate and colloidal silica and blend for about 15 minutes. Add one-fourth of the sodium stearyl fumarate and blend for about 4 minutes. Slug this blend using ½ inch flat-face punches and mill. Add the remainder of the sodium stearyl fumarate and blend for about 4 minutes. Compress the sodium warfarin granulation into tablets. Encapsulate this formulation with the use of a capsule filling machine such as the Zanasi AZ5, by placing one tablet along with a sufficient amount of aspirin granulation to equal one dosage unit into each capsule. It should be noted that the amount of lactose in this formulation is adjusted such that the total dosage form weight is 200 mg.

II. Sustained Aspirin Release

1. Sustained Release Aspirin Particles/Sodium Warfarin

These formulations involve the coating of aspirin microtablets, particles, granules, or non-pareils with a sustained-release material such as methacrylate ester copolymers (Eudragit®NE30D, Eudragit®RS30D and/or Eudragit®RL30D, Eudragit®RL and/or Eudragit®RS, all available from Röhm Pharma), organic-based ethylcellulose, aqueous-based ethylcellulose (Aquacoat®, FMC Corp.; Surelease®, Colorcon), or other appropriate material as known in the art to effect a sustained release of 3–12 hours. These coated entities can be additionally overcoated with a layer of low viscosity hydroxypropylmethylcellulose in order to guard against rupture of the sustaining layer upon compression. These microtablets, particles, granules, or non-pareils can optionally be additionally enteric coated with an enteric release polymer such as Aquateric®, Eudragit®L30D, or Eudragit®L and/or Eudragit®S to effect a sustained release in the intestine only. Another approach involves the use of a combination of polymers (such as Eudragit®NE30D and Eudragit®L30D) in a single coating to produce sustained release in the intestine. These layers can be applied by fluidized bed, coacervation-phase separation, pancoating, solids processor or other appropriate methods as known in the art. The coated aspirin is then mixed with appropriate excipients, and this blend is mixed with a sodium warfarin granulation and either placed into a capsule or compressed into a tablet. Alternatively, the sustained release aspirin blend can be compressed into a tablet or microtablets, which optionally may be additionally coated with an enteric layer, and placed into a capsule along with the sodium warfarin granulation. These two mixtures can also be processed in such a way as to produce a multilayer tablet with the aspirin and sodium warfarin existing in separate, distinct layers. These alternatives yield products which release the aspirin in a sustained manner. Additionally, contact between the aspirin and sodium warfarin within the product is minimized. The following is an example of a formulation of this type:

EXAMPLE 6

Sustained Release Aspirin/Sodium Warfarin Blend

| Component | Amount (mg) per Dosage Unit |
| --- | --- |
| Aspirin (coated with 3–15% Surelease ® (ethylcellulose)) | 164.95–188.24 (160.0 mg active) |
| Sodium Warfarin | 5.0 |
| Microcrystalline Cellulose | 184.76–208.05 |
| Sodium Starch Glycolate | 16.0 |
| Colloidal Silica | 1.0 |
| Sodium Stearyl Fumarate | 8.0 |
| To Total | 403.00 mg |

Prior to weighing, pass all ingredients though an appropriate screen as needed. Weight all ingredients and place the sustained release coated aspirin, one-half of the microcrystalline cellulose, colloidal silica and sodium starch glycolate into a twin-shell blender, and mix for about 15 minutes. Combine the sodium warfarin with the remaining microcrystalline cellulose, colloidal silica, and sodium starch glycolate and mix for about 15 minutes. Add one-half of the sodium stearyl fumarate to the sodium warfarin blend and blend for about 3 minutes. Slug this blend using ½ inch flat-face punches and mill. Combine the aspirin blend with the sodium warfarin granulation and mix for about 10 minutes in a twin-shell blender. Add the remaining sodium stearyl fumarate, mix for about 3 minutes and either compress the blend into tablets or place into capsules. It should be noted that the microcrystalline cellulose in this formulation is adjusted such that the total dosage form weight is 403.0 mg.

EXAMPLE 7

Sustained Release Aspirin Compressed Into A Tablet (Or Microtablets)/Sodium Warfarin In A Capsule Using the ingredients of Example 4, in like quantity, prior to weighing, pass all ingredients through an appropriate screen as needed. Weigh all ingredients and place the sustained release coated aspirin and one-half of the microcrystalline cellulose, sodium starch glycolate, and colloidal silica into a twin-shell blender and mix for about 15 minutes. Add one-half of the sodium stearyl fumarate and mix for about 5 minutes. Compress this mixture into a tablet or microtablets. Combine the sodium warfarin with the remaining microcrystalline cellulose, colloidal silica, and one-fourth of the sodium stearyl fumarate and mix for about 15 minutes. Slug this blend using ½ inch flat-face punches and mill. Add the remaining sodium stearyl fumarate and mix for about 5 minutes. With the use of a capsule filling machine such as the Zanasi AZ5, encapsulate this formulation by placing an aspirin tablet or microtablets and an amount of sodium warfarin granulation for one dosage unit into each capsule.

EXAMPLE 8

Sustained Release Aspirin/Sodium Warfarin In A Multilayered Tablet

| Component | Amount (mg) per Dosage Unit |
|---|---|
| Aspirin (coated with 3-15% Surelease ® (ethylcellulose)) | 164.95-188.24 (160.0 mg active) |
| Sodium Warfarin | 5.0 |
| Microcrystalline Cellulose | 369.26-392.55 |
| Sodium Starch Glycolate | 24.0 |
| Colloidal Silica | 1.5 |
| Sodium Stearyl Fumarate | 12.0 |
| To Total | 600.00 mg |

Prior to weighing, pass all ingredients though an appropriate screen as needed. Weight all ingredients and place the sustained release coated aspirin and one-half of the microcrystalline cellulose, sodium starch glycolate and colloidal silica into a twin-shell blender and mix for about 15 minutes. Add two-thirds of the sodium stearyl fumarate and mix for about 5 minutes. Combine the sodium warfarin with the remaining microcrystalline cellulose, sodium starch glycolate and colloidal silica and mix for about 15 minutes. Add one-sixth of the sodium stearyl fumarate and mix for about 5 minutes. Slug this blend using ½ inch flat-face punches, and mill. Add the remaining sodium stearyl fumarate and mix for about 5 minutes. Using a multilayer tablet machine such as the Manesty Layer Press (available from Thomas Engineering), compress the aspirin blend, followed by the sodium warfarin granulation, to produce a bilayer tablet.

2. Sustained-Release Matrix Tablet/Sodium Warfarin Within a Capsule

In this formulation a sustained release matrix tablet containing aspirin is first manufactured by methods known in the art, and this tablet is placed into a capsule along with a sodium warfarin granulation. The sustained release matrix is produced by mixing aspirin with various types of hydroxypropyl methylcellulose (HPMC) (Methocel ®K, Methocel ®J, Methocel ®E, all available from Dow Chemical), and hydroxypropyl ethylcellulose (Klucel ®, Dow Chemical), either alone or in combination, along with appropriate excipients. When using Methocel ®K or Methocel ®J having a 2% viscosity greater than 800 cps either alone or in combination, the combined amount of Methocel ®K and/or Methocel ®J should be greater than 25.8% of the total dosage form weight. If the Methocel ®K or Methocel ®E or a combination thereof have a 2% viscosity of less than 800 cps, then the hydroxypropyl content is less than 9% of the total dosage form weight. Alternatively, the Methocel ®K and/or Methocel ®J can be mixed with a non-HPMC cellulose ether provided that the non-HPMC cellulose ether comprises greater than 30% of the entire polymer mixture.

The matrix tablet can additionally be coated with a low-viscosity polymer (e.g., hydroxypropyl methylcellulose) which works in concert with the polymer within the matrix to yield a sustained release.

In all cases drug release takes place over about a 3-12 hour period. The sustained release tablet is then placed into a capsule along with a sodium warfarin granulation. Alternatively, the aspirin tablet can be coated by methods known in the art with an enteric coating material such as Eudragit ®L30D, Eudragit ®L, Eudragit ®S, Aquateric ®, or other materials known in the art. The net result of this option is to effect a sustained release in the intestine only.

EXAMPLE 9

Sustained-Release Matrix Tablets/Sodium Warfarin Within A Capsule

| Component | Amount (mg) per Dosage Unit |
|---|---|
| Aspirin | 160.0 |
| Methocel ® E4M Premium CR | 109.95 |
| Sodium Warfarin | 2.0 |
| Lactose | 128.07 |
| Dicalcium Phosphate | 125.32 |
| Colloidal Silica | 2.34 |
| Sodium Stearyl Fumarate | 12.32 |
| To Total | 540.0 mg |

Prior to weighing, pass all ingredients through an appropriate screen as needed. Mix the aspirin with the lactose, Methocel ® and one-half of the colloidal silica for about 15 minutes in a twin-shell blender. Add two-thirds of the sodium stearyl fumarate and mix for an additional 5 minutes. Compress this blend into tablets (135.77 mg each) such that three tablets yields aspirin sufficient for one dosage unit (160 mg total aspirin).

Mix the sodium warfarin with the dicalcium phosphate and remaining colloidal silica for about 15 minutes. Add one-sixth of the sodium stearyl fumarate and mix for about 5 minutes. Slug this blend using ½ inch flat-face punches and mill. Add the remaining sodium stearyl fumarate and mix for about an additional 5 minutes. Encapsulate this formulation by placing sodium warfarin granulation to equal one dosage unit and three aspirin tablets into each capsule with the use of a capsule filling machine such as the Zanasi AZ5.

The aspirin tablet component of this formulation was manufactured (8/32 inch tablets, hardness 10-12 SCU), and drug release was assessed. The dissolution apparatus and media used were the same as that described in Example 2 with the exception that 500 ml of 0.1 N HCl was used during the first 2 hours, followed by adjustment of the pH to 7.5 with the addition of 250 ml of tribasic sodium phosphate. Dissolution data are shown in Table III.

TABLE III

Aspirin Release From Matrix Tablets Manufactured In Accordance With Example 9

| Time (hour) | pH | Average (n = 3) % Released |
|---|---|---|
| 1 | 1.0 | 38.3 |
| 2 | 1.0 | 56.5 |
| 3 | 7.5 | 75.3 |
| 4 | 7.5 | 84.7 |
| 5 | 7.5 | 95.2 |
| 6 | 7.5 | 99.6 |

By substituting non-aspirin NSAID agents, ticlopidine, thromboxane receptor antagonists or thromboxane synthetase inhibitors for aspirin in the above examples, other formulations within the scope of this invention can be prepared. Additionally, other oral anticoagulant agents such as coumarin derivatives (for example phenindione, bishydroxycoumarin (dicumarol) and phenprocoumon can be substituted for warfarin in the above examples, rendering formulations within the scope of this invention.

Utility

The potential for enhanced efficacy and an improved margin of safety by combining a low-dose of an oral anticoagulant, such as warfarin and a low-dose of platelet inhibitor agents, in general or non-steroidal anti-inflammatory agents, particularly aspirin, is supported by the previous clinical experience with the use of each (or a closely related compound) individually at high doses in the prevention and treatment of acute coronary ischemic syndromes and ischemic cerebrovascular disease, as well as by certain suggestive evidence from their simultaneous administration.

Clinical studies using oral anticoagulants alone, including crystalline sodium warfarin, have provided evidence of their efficacy in the treatment or secondary prevention of coronary artery disease. Of three published, randomized, controlled trials of the treatment of acute myocardial infarction, oral anticoagulation significantly reduced overall mortality and the frequency of reinfarction in one study. Of the four published large, randomized, controlled trials of oral anticoagulants in the secondary prevention of myocardial infarction, three suggested a reduction in the incidence of reinfarction and early mortality. One additional study, the Warfarin Reinfarction Study, has also recently demonstrated a significant reduction in mortality, reinfarction, and stroke in people with a previous myocardial infarction who were treated with warfarin as compared to those treated with placebo.

The results of studies utilizing acetylsalicylic acid (ASA) alone in the prevention and treatment of coronary artery disease have also been promising. In patients with unstable angina, ASA has been demonstrated to reduce the incidence of subsequent myocardial infarction and mortality in two large, randomized, double-blind, placebo-controlled clinical studies. In addition, ASA has been approved for use in the secondary prevention of myocardial infarction, based on a data from several trials which, when pooled, suggested a reduction in reinfarction and mortality. Finally, two recent studies evaluating ASA in the primary prevention of coronary artery disease have reported either a dramatic or inconsequential benefit; ASA has not as yet been approved for this indication.

In addition to their utility in coronary artery disease, agents that inhibit platelet function such as ASA and ticlopidine have been shown to be effective in the prevention of stroke in people with cerebrovascular disease. Pooled data from nine randomized trials have provided overwhelming evidence of the efficacy of ASA alone in reducing the risk of completed stroke in people with transient ischemic attacks (TIAs). Recently, ticlopidine alone has also been demonstrated to have efficacy in treating TIAs.

The postulate that warfarin and ASA in combination will afford an efficacy advantage over either agent alone is based on recent angioscopy data and is supported by both pilot studies and anecdotal reports. Based on the direct visualization of ulcerated atherosclerotic plaques within the coronary arteries, Forrester et al. have proposed two distinct pathologic cycles of platelet-dependent and thrombus-dependent injury and repair in acute coronary ischemic syndromes which strongly suggest a potential benefit of the two agents when used in combination. This pathophysiologic pattern can be extrapolated to the cerebrovascular system, as well. Recent pilot data in patients with unstable angina revealed a benefit in patients receiving both heparin (an anticoagulant)/warfarin and ASA, when compared to those receiving either agent alone. Additionally, patients with prosthetic heart valves, receiving both agents simultaneously for the prevention of stroke, have been noted to have a remarkably low incidence of myocardial infarction.

There is a need for a therapeutic approach to the acute coronary ischemic syndromes and ischemic cerebrovascular diseases which takes into account the diverse pathophysiologic makeup of such diseases and which includes therapeutic agents for ameliorating each of these pathophysiological components. A combination product containing a low dose of warfarin and a low dose of a platelet-inhibiting agent such as a non-steroidal antiinflammatory agent, and particularly aspirin, can provide such an approach. In addition, by administering low doses of each, the incidence of GI and other side effects associated with the concurrent administration of these drugs at higher doses is significantly reduced and the patient is offered a convenient single dosage form for the once-daily, lifelong administration of these two medications. It is generally accepted that increased convenience to the patient results in an increase in compliance. Furthermore, a combination product, available by prescription only, will give the physician greater dose control than if the patient were to independently select from the various dosages and formulations and purchase aspirin over-the-counter. The combination products of the present invention will also reduce the likelihood of patient confusion often associated with concurrent dosing of medication when it is not available in a combination product.

What is claimed is:

1. A method for the prevention or treatment of a first or recurrent myocardial infarction or a first or recurrent stroke in a mammal comprising administering to the mammal in an amount effective for prevention or treatment of a first or recurrent myocardial infarction or first or recurrent stroke, a combination of active ingredients comprising warfarin or a pharmaceutically acceptable salt thereof and a platelet inhibitory agent selected from the group consisting of acetylsalicylic acid, a non-steroidal antiinflammatory agent and ticlopidine, said active ingredients being present in a ratio which provides therapeutic effectiveness with limited dose related side effects, whereby the warfarin has an inhibitory effect on thrombus formation and the platelet inhibitory agent has an inhibitory effect on platelet aggregation.

2. A pharmaceutical composition having an inhibitory effect on thrombus formation and platelet aggregation said composition comprising a suitable pharmaceutical carrier and a combination of active ingredients consisting essentially of warfarin or a pharmaceutically acceptable salt thereof present in an amount to be delivered of about 0.5–10.0 mg and acetylsalicylic acid present in an amount to be delivered of about 10.0–325.0 mg.

3. A composition of claim 2 wherein the warfarin or a pharmaceutically acceptable salt thereof is present in an amount to be delivered of about 1.0–7.5 mg and the acetylsalicylic acid is present in an amount to be delivered of about 20.0–325.0 mg.

4. A composition of claim 3 wherein the warfarin or a pharmaceutically acceptable salt thereof is present in an amount to be delivered of about 1.0–5.0 mg and the acetylsalicylic acid is present in an amount to be delivered of about 40.0-162.5 mg.

5. A composition of claim 2 wherein the combination is in a dosage form which provides minimal physical contact between the warfarin or a pharmaceutically acceptable salt thereof and the acetylsalicylic acid.

6. A composition of claim 5 wherein to achieve the minimal physical contact the acetylsalicylic acid component is enteric coated.

7. A composition of claim 5 wherein to achieve the minimal physical contact the acetylsalicylic acid component is coated with sustained release material and additionally further enteric coataed.

8. A pharmaceutical composition having an inhibitory effect on thrombus formation and platelet aggregation said composition comprising a suitable pharmaceutical carrier and a combination of active ingredients consisting essentially of warfarin or a pharmaceutically acceptable salt thereof present in an amount to be delivered of about 0.5-10.0 mg and a non-steroidal antiinflammatory agent selected from the group consisting of piroxicam, present in an amount to be delivered of about 5.0-50.0 mg, indomethacin, present in an amount to be delivered of about 20.0-100.0 mg, naproxen, present in an amount to be delivered of about 20.0-100.0 mg, diclofenac, present in an amount to be delivered of about 20.0-100.0 mg, and sulfinpyrazone, present in an amount to be delivered of about 20.0-100.0 mg.

9. A pharmaceutical composition having an inhibitory effect on thrombus formation and platelet aggregation said composition comprising a suitable pharmaceutical carrier and a combination of active ingredients consisting essentially of warfarin or a pharmaceutically acceptable salt thereof present in an amount to be delivered of about 0.5-10.0 mg and ticlopidine present in an amount to be delivered of about 100.0-750.0 mg.

10. A composition of claim 9 wherein the warfarin or a pharmaceutically acceptable salt thereof is present in an amount to be delivered of about 1.0-7.5 mg and the ticlopidine is present in an amount to be delivered of about 200.0-600.0 mg.

11. A composition of claim 10 wherein the warfarin or a pharmaceutically acceptable salt thereof is present in an amount to be delivered of about 1.0-5.0 mg and the ticlopidine is present in an amount to be delivered of about 250.0-500.0 mg.

12. A composition of claim 2 in a tablet dosage form.

13. A composition of claim 2 in a capsule dosage form.

14. A composition of claim 2 in a caplet dosage form.

15. A composition of claim 2 in a suppository dosage form.

16. A pharmaceutical composition having an inhibitory effect on thrombus formation and platelet aggregation, said composition comprising:
 (a) about 40.0 mg to about 162.5 mg of active acetylsalicylic acid which is optionally coated with an appropriate enteric release polymer;
 (b) about 1 mg to about 7.5 mg of warfarin or a pharmaceutically acceptable salt thereof which is optionally coated with an appropriate polymer to minimize contact between the active components of (a) and (b); and
 (c) a pharmaceutically acceptable carrier.

17. A composition of claim 16 wherein the acetylsalicylic acid component is coated with an enteric release polymer selected from the group consisting of cellulose acetate phthalate or methacrylic acid copolymers.

18. A composition of claim 16 wherein the warfarin or a pharmaceutically acceptable salt thereof is coated with a low-viscosity grade of hydroxypropyl methylcellulose.

19. A composition of claim 16 wherein the acetylsalicylic acid component is coated with an enteric release polymer selected from the group consisting of cellulose acetate phthalate or methacrylic acid copolymers and the warfarin or a pharmaceutically acceptable salt thereof is coated with a low-viscosity grade of hydroxypropyl methylcellulose.

20. A pharmaceutical composition having an inhibitory effect on thrombus formation and platelet aggregation, said composition comprising:
 (a) about 40.0 mg to about 162.5 mg of active acetylsalicylic acid which is optionally coated with an appropriate enteric release polymer;
 (b) about 1 mg to about 7.5 mg of warfarin which is optionally coated with an appropriate polymer to minimize contact of the active components of steps (a) and (b); and
 (c) a pharmaceutically acceptable carrier.

21. A composition of claim 20 wherein the acetylsalicylic acid is coated with an appropriate sustained release polymer such that release occurs over about 3 to 12 hours.

22. A composition of claim 21 wherein the sustained release polymer is selected from the group consisting of methacrylate ester copolymers, organic-based ethylcellulose or aqueous-based ethylcellulose.

23. A composition of claim 20 wherein the acetylsalicylic acid component is additionally coated with an appropriate enteric release polymer.

24. A composition of claim 23 wherein the enteric release polymer is a methacrylic acid copolymer.

* * * * *